United States Patent [19]
Tahara et al.

[11] Patent Number: 5,116,736
[45] Date of Patent: May 26, 1992

[54] METHOD FOR THE QUANTITATIVE DETERMINATION OF MICRO-ORGANISMS OR PYROGENS

[75] Inventors: Shu Tahara, Kyoto; Nariyoshi Kawabata, Osaka; Akira Kojima, Kyoto; Shigeru Fukushima, Ootsu, all of Japan

[73] Assignee: Shimadzu Corporation, Kyoto, Japan

[21] Appl. No.: 273,945

[22] Filed: Nov. 21, 1988

[30] Foreign Application Priority Data

Feb. 19, 1988 [JP] Japan ............................ 63-38341
Jun. 30, 1988 [JP] Japan ........................... 63-164139

[51] Int. Cl.⁵ .................... G01N 33/487; G01N 31/12
[52] U.S. Cl. ........................................ 435/39; 435/34; 436/146; 436/175; 436/177; 436/825
[58] Field of Search .................. 435/39, 261, 800, 34; 436/45, 146, 158, 175, 176, 177, 825; 422/78, 93

[56] References Cited

U.S. PATENT DOCUMENTS

| | | | |
|---|---|---|---|
| 3,647,392 | 3/1972 | McGinnis | 23/254 E |
| 3,964,868 | 6/1976 | DiCola et al. | 23/253 PC |
| 4,095,951 | 6/1978 | DiCola et al. | 23/253 PC |
| 4,285,669 | 8/1981 | Itoh | 23/230 PC |
| 4,866,270 | 9/1989 | Hall et al. | 250/282 |

Primary Examiner—David L. Lacey
Assistant Examiner—David Redding
Attorney, Agent, or Firm—Sandler, Greenblum & Bernstein

[57] ABSTRACT

A method for the quantitative determination of micro-organisms or pyrogens which comprises introducing a prescribed amount of a test liquor containing micro-organisms or pyrogens into a total carbon analyzer to obtain a total carbon value A, while removing micro-organisms or pyrogens from the prescribed amount of the same test liquor and introducing the resultant into a total carbon analyzer to obtain a total carbon value B, subtracting the total carbon value B from the total carbon value A and determining micro-organisms or pyrogens basing upon the resulting value, and an apparatus suitable for conducting the method.

8 Claims, 5 Drawing Sheets

METHOD FOR THE QUANTITATIVE DETERMINATION OF MICRO-ORGANISMS OR PYROGENS

BACKGROUND OF THE INVENTION

1. Field of the Invention

The present invention relates to a method and an apparatus for the quantitative determination of micro-organisms or the like. More particularly, it relates to a method and an apparatus for the quantitative determination of micro-organisms or pyrogens in a liquor, which are simple and trustworthy.

2. Description of the Prior Art

Determination (quantitative determination) of the amount of micro-organisms in various media is important for public sanitation or quality control in, not only the fields of positively utilizing micro-organisms, such as fermentation, brewing, etc., but also various other fields such as medical treatment, food stuffs, analysis, etc.

As methods for the quantitative determination of such micro-organisms, the following methods have been generally known, hitherto;

1 Visual estimation method (so-called colony method); a method for the quantitative determination of micro-organisms wherein a test liquor containing micro-organisms is, after subjecting to a dyeing treatment, put on a slide glass, the number of micro-organisms in the visual field is counted by a microscope, and the amount of the micro-organisms is determined on the basis of said number.

2 Optical estimation method (so-called OD method); a method for the quantitative determination of micro-organisms wherein a test liquor containing micro-organisms is subjected to irradiation of light to find out its turbidity and the amount of the micro-organisms is determined on the basis of said turbidity.

3 Dilution culture method; a method for the quantitative determination of micro-organisms wherein a prescribed dilution series of a sample liquor containing micro-organisms is prepared, each diluted liquor is inoculated and cultivated in a culture tube, and the amount of the micro-organisms is determined statistically on the basis of the state of their growing.

On the other hand, pyrogens are known as substances which cause difficulties in various media just like micro-organisms, though they are not micro-organisms, and quantitative determination of such pyrogens is also desired for public sanitation or quality control. Especially, quantitative determination of pyrogens in distilled water, such as distilled water for injection, distilled water for dialysis, etc., is important for public sanitation.

As methods for quantitative determination or test methods of such pyrogens, a method relying on the elevation of body temperature of rabbits that is caused by injection to the rabbits of a subject sample (the Japanese Pharmacopoeia: test methods for pyrogens, is referred to) is widely used. However, this method involves inconveniences that the results are often influenced by the individual difference in sensibility among the rabbits and, moreover, observation of the changes in body temperature and breeding of the animals are required over a long time period. Accordingly, the so-called Limulus test,is recently remarked as a method for the quantitative determination and evaluation of pyrogens, wherein the selective reaction between a blood-corpuscle extract of Limulus and a pyrogen is utilized and the amount of the pyrogen is determined on the basis of the gelation degree by said reaction or the absorbance after diazotization of p-nitroaniline which may produce from said reaction performed in the presence of a color-forming synthetic substrate (refer to a Japanese Journal "Kan-Tan-Sui" 12(4): 523–528, 1986, etc.).

However, the hitherto known methods for the quantitative determination of micro-organisms as mentioned above involve various problems that the operation for determination requires a long time and, as well, is troublesome and requests skillfulness, that the range of the amount of micro-organisms capable of quantitative determination is narrow and the results of determination are not necessarily trustworthy, and also that they are not suitable for continuous determination.

On the other hand, the above-mentioned, hitherto used methods for quantitative determination and evaluation of pyrogens also involve problems that the operation requires a long time and, as well, is troublesome and requests skillfulness, that they use a costly Limulus extract, and also that they are not suitable for continuous determination.

The present invention has been accomplished in view of such circumstances with the purpose of providing a method and an apparatus for quantitative determination of the amount of micro-organisms or pyrogens, which are simple and trustworthy and, as well, suitable for continuous determination.

SUMMARY OF THE INVENTION

Thus, the present invention provides a method for the quantitative determination of micro-organisms or pyrogens which comprises introducing a prescribed amount of a test liquor containing micro-organisms or pyrogens into a total carbon analyser to obtain a total carbon value A, while removing micro-organisms or pyrogens from the prescribed amount of the same test liquor and introducing the resultant into a total carbon analyser to obtain a total carbon value B, subtracting the total carbon value B from the total carbon value A and determining micro-organisms or pyrogens basing upon the resulting value.

Further, the present invention provides an apparatus for the quantitative determination of micro-organisms or pyrogens, comprising a storage portion for test liquor, a supply channel I and a supply channel II providing a means for removing micro-organisms or pyrogens, which are connected to the storage portion, a measuring passage providing a liquor measuring means to be connected to the supply channels I and II through a channel switching means, and a total carbon analyser connected to the measuring passage.

According to the method and the apparatus of the present invention, the amount of micro-organisms or pyrogens can be quantitatively determined quickly and simply. Further, the quantitative determination according to the present invention, which is performed on the basis of TC values, is trustworthy and easily applicable also to continuous determination.

DETAILED DESCRIPTION OF THE PREFERRED EMBODIMENT

The most characteristic feature of the present invention resides in using a total carbon analyser for quantitative determination of micro-organisms or pyrogens. As the total carbon analyser, any total carbon analyser of of type wherein carbon-containing substances are oxidized to produce carbon dioxide and the amount of the carbon dioxide is detected by a non-diffractive type infrared ray detector, an electric conductivity meter, a thermal conductivity detector, or the like, may be used. That is, various total carbon analysers which are commercially available as the so-called TOC meter or TC meter can be used. As methods for oxidizing the carbon-containing substances, there are two types, i.e., wet oxidation methods by UV oxidation or by oxidation with an oxidizing agent such as potassium peroxosulfate solution etc., and combustion oxidation methods. However, it is preferable to employ those combustion oxidation methods, according to which the oxidation is performed most strongly and surely. In such combustion oxidation methods, an oxidation catalyst such as platinum black may be used. The combustion is suitably carried out in a combustion tube heated at 680°–950° C. in an atmosphere of highly pure air or oxygen gas. On the other hand, the detection of carbon dioxide is suitably performed by using a non-diffractive infra-red ray (NDIR) detector, in view of its high trustworthiness and operational easiness.

Another characteristic feature of the present invention resides in utilizing, for the quantitative determination of micro-organisms or pyrogens, a treated liquor free from the micro-organisms or pyrogens which is obtained by subjecting the test liquor to a removal treatment. The treatment mentioned above means a treatment for removing micro-organisms or pyrogens from the test liquor.

As the treatment for removing micro-organisms or pyrogens, any method suited to remove the micro-organisms or pyrogens, such as membrane filtration treatment method, adsorption treatment method, absorption treatment method, centrifugal treatment method, etc.

The filtration treatment or the adsorption treatment is suitably performed by allowing a test liquor to pass through a filtration removal means or an adsorption removal means.

Especially, the filtration treatment of micro-organisms is suitably performed with a filter having a pore size capable of trapping the minimum micro-organisms intended for determination, among the micro-organisms possibly existing in a test liquor. As the filter, porous filter, membrane filter, etc., having a pore size of ultra-filtration grade are usually suitable. As materials for the above-mentioned porous filter, organic substances such as organic high-polymer, vital fibers, etc., inorganic substances such as glass, ceramics, etc., and their composites are mentioned. The filter may be of various forms such as flat membrane, cylinder, fiber, hollow fiber, etc., and of any constitutions such as symmetry, asymmetry, mosaic, etc. The pore size of the filter may be, for example, a degree of 0.45 μm or less for the separation by filtration of micro-organisms and a degree of 0.2 μm or less for the separation by filtration of pyrogens. These degrees, however, are not limited thereto. However, any pore size selected must be one that allows organic substances, except those which are the object of the determination, to pass through the filter. Further, on performing the filtration treatment, it is preferable to use the above-mentioned filter after subjecting it beforehand to a treatment with ultrasonic waves in super pure water. By this ultrasonication treatment, organic substances (components of the material) which may elute from the filter itself are removed beforehand and, as a result, error of determination resulting from the use of the filter can be decreased.

As means for the adsorption treatment, charged membranes or ion-exchange resins are used, and insoluble pyridinium type resins such as cross-linked poly-N-alkyl-4-vinyl pyridinium halide, etc. are effective.

The centrifugal treatment can be performed with a conventionally used centrifuge. In the centrifugal treatment, a too low rotation speed would cause an insufficient separation of micro-organisms or pyrogens from a test liquor and bring about difficulties in obtaining a treated liquor free from the micro-organisms or pyrogens, as the supernatant liquid, while a too high rotation speed would cause cell destruction of micro-organisms or pyrogens and bring about a lowering of the trustworthiness of the quantitative determination. From such point of view, the centrifugation for separating micro-organisms is effected at a rotation speed suitably of 2000–5000 rpm, and preferably of 3000–4500 rpm. Although there is no special limitation in the time for the centrifugal separation (rotation time), a rotation time of 5–30 minutes or so is usually suitable. According to such centrifugal treatment, errors of quantitative determination which may arise in the above-mentioned filtration treatment method and adsorption treatment method because of the elution of the material components, can be avoided. Therefore, it is possible according to the centrifugal treatment to perform a trustworthy quantitative determination even with respect to a low content specimen liquor of micro-organisms or pyrogens. Thus, the centrifugal treatment method is the most preferable embodiment.

By the way, it is suitable in view of the convenience for the calculation in quantitative determination to use the treated liquor free from micro-organisms (or pyrogens) in the same amount as that of the test liquor containing the micro-organisms (or pyrogens).

Figure 6:
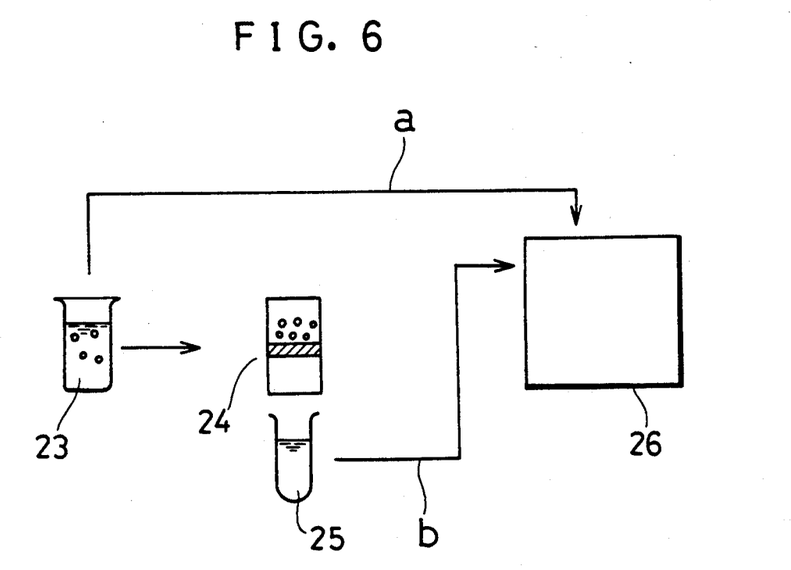
FIG. 6 is a flow diagram of the method of the present invention using a membrane filtration treatment.

FIG. 6 is a flow diagram of the present method using a membrane filtration treatment in which a test liquor at 23, a filtration removal means at 24, a filtrate (treated liquor) at 25 and a total carbon analyser at 26 are shown. As is shown in this figure, the present method consists essentially of a step (a) of determining a TC value A by introducing directly a test liquor 23 into a total carbon analyser 26 and a step (b) of determining a TC v value B by introducing a treated liquor 25 into the analyser 26.

In a test liquor containing micro-organisms, organic substances (sugars such as glucose) desired from the culture medium, contaminating organic substance (organic amines and soluble organic high polymer), inorganic carbon compounds (such as dissolved $CO_2$, carbonates, carbonic ion, etc.), or the like, may coexist with the micro-organisms. Therefore, it is difficult to determine the amount of micro-organisms exactly on the basis of a TC (total carbon) value A obtained by introducing such test liquor directly into the above-mentioned total carbon analyser. It is also difficult to determine the amount of pyrogens exactly on the basis of a TC value A obtained by introducing a test liquor directly into the total carbon analyser, since pyrogens are usually contained in a test liquor in a very small amount and other organic components may often coexist in the test liquor with them.

According to the present invention, a TC value B for a treated liquor free from micro-organisms (or pyrogens) is further determined, and a value obtained by subtracting the TC value B from the TC value A is calculated. Although micro-organisms (or pyrogens) are substantially removed by the above-mentioned filtration treatment or adsorption treatment etc., other coexisting organic substances and inorganic carbon compounds are not removed by such treatment but remain in the treated liquor free from micro-organisms (or pyrogens). Therefore, the value substantially corresponding to the amount of micro-organisms (or pyrogens) contained in the test liquor. Thus, the amount of micro-organisms (or pyrogens) can be determined exactly on the basis of this value.

According to the present invention, quantitative determination of micro-organisms (or pyrogens) can be conveniently performed by using an apparatus wherein a supply channel I having no means for removing micro-organisms or pyrogens and a supply channel II having a means for removing micro-organisms or pyrogens (such as means for the removal by filtration or means for the removal by adsorption) are constituted so that either one of them may be connected through a channel switching means to a liquor measuring means from which a prescribed amount of each of the test liquor and the treated liquor is introduced to a total carbon analyser. The use of such apparatus is preferable from the view-point of automatic operation, continuous operation and the like. As for the liquor measuring means, it is preferred from the point of automatic and continuous operation to use a liquor measuring means of valve changing-over type, although an automatic measuring means of micro syringe type may also be mentioned.

It is also possible to effect a perfect continuous determination according to the present invention, by determining each of the TC value A and the TC value B simultaneously, using two NDIRs.

EXAMPLE

Figure 1:
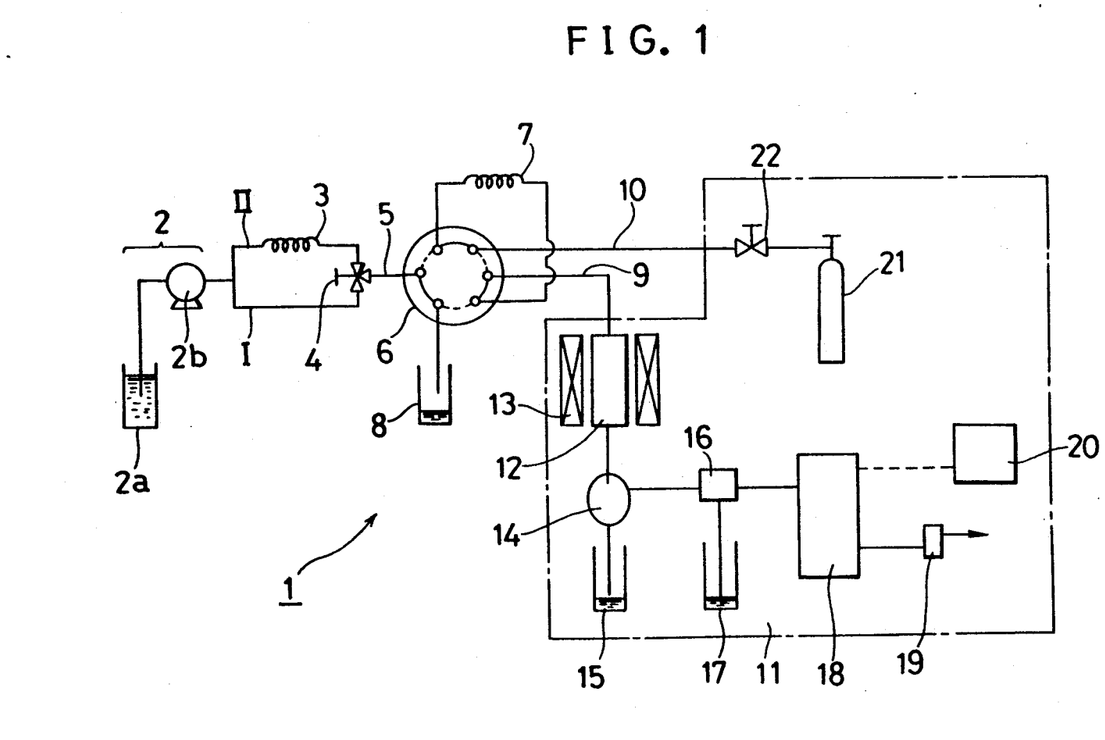
FIG. 1 is a block diagram showing an example of the apparatus for continuously carrying out the quantitative determination method for micro-organisms or pyrogens of the present invention.

In FIG. 1, an Example of the apparatus for quantitative determination of micro-organisms or pyrogens, for the method of the present invention is shown as numeral 1. In this figure, a supply channel I and a supply channel II are connected in branched form with test liquor supply portion 2 which consists of a storage tank 2a for storing the test liquor and a liquor-transporting pump 2b. The supply channel II is provided with a filtration means for removing micro-organism (or pyrogens) 3 comprising an ultrafilter. The down streams from the supply channels I and II are collected at a three-way valve (channel switching means) 4, and the test liquor or the treated liquor is supplied through the supply channels I or II to a measuring channel 5, by changing-over of the valve 4.

To the measuring channel 5, a high voltage six-way changing-over valve 6 is connected. The test liquor or the treated liquor transported, by changing-over of the value 6, to either one of an exhaust liquor tank 8 and a liquor-measuring means 7 constituted by a pipe of a certain length. The liquor introduced into the liquor-measuring means 7 is led into a total carbon analyser 11 through an inlet pipe 9, by changing-over of the valve 6.

The total carbon analyser 11 is constituted by a combustion tube 12 made of quartz glass, and holding a catalyst carrier layer (inside diameter: 12 mm, length: 90 mm) comprising quartz wool coated with platinum black, an electric heater 13, a drain separator 14, an electronic cooler 16 and a non-diffractive type infra-red ray detector 18, connected in this succession, and provided with a highly pure air bomb 21 for supplying carrier gas (a pure air having CH content, CO content and $CO_2$ content, as impurities, of each 1 ppm or less). The figure also shows a carrier gas supply channel at 10, drain pots at 15 and 17, a flow meter at 19, an operation division at 20, and a flow rate controlling valve at 22.

Operation of quantitative determination of micro-organisms, by using the above-mentioned apparatus 1, is explained hereinafter.

At first, a test liquor containing a micro-organism is directly introduced, to the measuring channel 5, by setting the three-way valve 4 at the supply channel I side and driving the liquor-transporting pump 2b. Then, the high voltage six-way changing-over valve 6 is changed-over from the solid line side to the dotted line side, and the test liquor is introduced to the liquor-measuring means 7 to fulfill it after a certain time. Then, the valve 6 is changed-over to the solid line side. The test liquor in the liquor-measuring means is sent, by pressure of a carrier gas comprising the air supplied from the bomb 21, to the combustion tube 12 heated at high temperature, where the micro-organisms and organic impurities are burnt and oxidized into carbon dioxide. The moisture generating as by-product of the combustion oxidation is removed by gas-liquid separation with the drain separator 14 and the electronic cooler 16 (cooled at 2° C). The carbon dioxide produced by the combustion oxidation is transported to the non-diffractive infra-red ray detector 18, together with the carbon dioxide resulting from thermal decomposition of carbonates, etc., and the carbon dioxide dissolved in the liquor. Absorbance of carbon dioxide is detected by the detector 18 and, on the basis of the detected output, the TC value A is calculated at the operation division 20 and put on record.

Next, the three-way valve 4 is changed-over to the supply channel II side, and a treated liquor free from micro-organisms obtained by allowing a test liquor to pass through the filtration means 3 is introduced to the measuring channel 5. Then, a prescribed amount of liquor from the channel 5 is introduced to the combustion tube 12 in the same manner as described above. Hereupon, micro-organisms do not exist substantially in the test liquor. However, organic impurities are not removed from the test liquor by the above filtration means 3. Such organic substances are burnt and oxidized into carbon dioxide, and its absorbance is detected in total with that of other carbon dioxide. On the basis of the total absorbance thus detected, the TC value B is calculated at the operation division 20 and put on record.

The value obtained by subtracting the TC value B from the TC value A corresponds to the amount of micro-organisms. Therefore, micro-organisms can be quantitatively determined by this value as a carbon amount directly and, by preparing beforehand a calibration curve of carbon amounts vs. micro-organism concentrations (such as weight concentrations, population concentrations, etc.), the amount of micro-organisms can be determined in various units on the basis of this value.

Example 1

Quantitative determination of micro-organisms

Using the above apparatus, quantitative determination of a micro-organism (lactic acid bacilli) was effected under the following conditions:

Conditions for combustion oxidation

Flow rate of carrier gas 150 ml/minute
Temperature of heating 680° C.

Test liquor

The test liquor was prepared by intermixing approx. 5.0 mg of lactic acid bacilli into 1 l of physiological salt solution (containing glucose corresponding to approx. 1000 ppm TC). The test liquor was not free from pyrogens.

Ultrafilter

An ultrafilter holding an ultrafiltration membrane comprising a membrane filter made of cellulose (pore diameter: 0.2 μm, outside diameter: 2.5 mm) was used after sterilization. Filtering pressure was approx. 0.1 Kg/cm$^2$.

The amount of the liquor injected for determination of TC was 5 μl. Calibration of TC value was effected by the use of potassium hydrogenphthalate standard value of 640 ppm.

Figure 2:
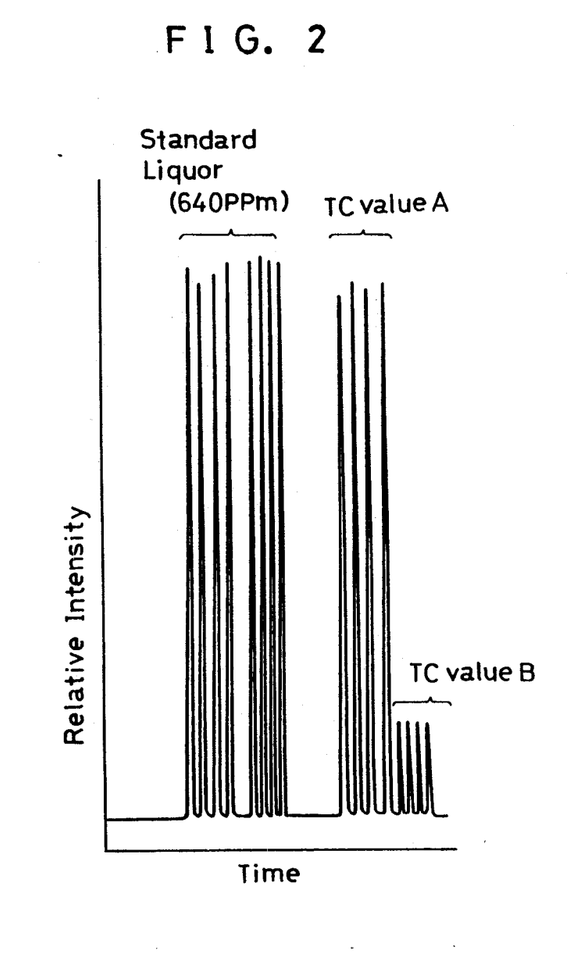
FIG. 2 is a graph illustrating an analytical chart obtained in an example of the present invention.

The results are shown in FIG. 2. The TC value A was one corresponding to 603.0 ppm TC, and the TC value B was one corresponding to 107.7 ppm TC. Therefore, it follows that lactic acid bacilli in the test liquor corresponds to 495.3 ppm TC. Further, the TC value B which was in good correspondence with the background (physiological salt solution) of approx. 100 ppm, showed that the removal ratio of lactic acid bacilli by the ultrafilter was good.

Example 2

Quantitative determination of pyrogens

Using the above apparatus of FIG. 1, quantitative determination of a pyrogen was effected. The test liquor used was one containing a prescribed amount of endotoxin as pyrogen, which was prepared by dissolving a prescribed amount of a standard pyrogen (USP Reference endotoxin, EC-5) in an endotoxin-free standard solution.

With regard to pyrogen-containing liquors of various concentrations, the TC value A and the TC value B were determined in the same manner as the above described quantitative determination method for micro-organisms and converted into endotoxin concentrations. The time required for each determination was within 5 minutes.

Figure 3:
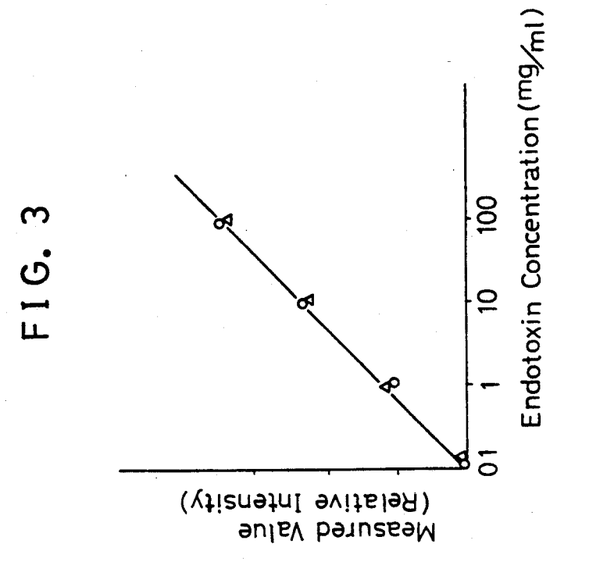
FIG. 3 is a graph illustrating results of analysis obtained in an example of the present invention.

The results are shown in FIG. 3, in contrast with the values obtained by the conventional Limulus test.

Thus, it is evident from the FIG. 3 that the quantitative determination according to the present invention can be effected with good linearity in response and with the same accuracy as Limulus test, with regard to pyrogens. In the figure, the plot -o- shows the results of the method of this invention and the plot -Δ- shows the results of Limulus test.

By the way, the same results as mentioned above were obtained with regard to pyrogen, when a reverse osmotic membrane (cellulose triacetate membrane; outside diameter: 90 mm, length: 420 mm, permeable amount of water: 0.018 m$^3$/hr) or an ultrafiltration membrane of polysulfone series (outside diameter: 40 mm, length: 350 mm, authorized fractional molecular weight: 6000, permeable amount of water: 0.035 m$^3$/hr) was used instead of the membrane filter in the ultrafilter.

Referential Example 1

Quantitative determination of micro-organisms

The samples were prepared by intermixing and suspending a suitable amount of each of the following micro-organisms (twelve kinds of bacteria and two kinds or yeasts) in 1 l of physiological salt solution.

| Micro-organisms: | | |
|---|---|---|
| | Alcaligenes faecalis | (a), |
| | Achromobacter polymorph | (b), |
| | Arthrobacter atrocyaneus | (c), |
| | Bacillus subtilis | (d), |
| | Escherichia coli B | (e), |
| | Escherichia coli K-12 | (f), |
| | Escherichia coli Najjar | (g), |
| | Pseudomonas aeruginosa | (h), |
| | Klebsiella pneumoniae | (i), |
| | Salmonella typhimurium | (j), |
| | Staphylococcus aureus | (k), |
| | Streptcoccus sp. | (l), |
| | Candida utilis | (m), |
| | Saccharomyces cerevisiae | (n). |

Preparation of a test liquor for determination of TC

Each of the sample prepared as described above was filtrated by means of the following ultrafiltration means, and the filtrated substance was collected with super pure water to prepare a micro-organism-containing test liquor.

Ultrafiltration means

A disposable filter made of polytetrafluoroethylene having an outside diameter of 25 mm and a pore diameter of 0.45 μm was used, after subjecting it to an ultrasonication treatment in super pure water for 10 minutes or more, prior to each determination.

With regard to the test liquors for TC determination thus prepared, quantitative determination of micro-organisms was effected by means of a total carbon analyser (corresponding to 11 in the figure) under the following conditions.

Conditions for combustion oxidation

Flow rate of carrier gas 150 ml/minutes
Temperature of heating 680° C.

The amount of the liquor injected for determination of TC was 10 ml. Calibration of TC value was effected by a standard liquor containing 200 ppm. of potassium hydrogenphthalate.

Figure 4:
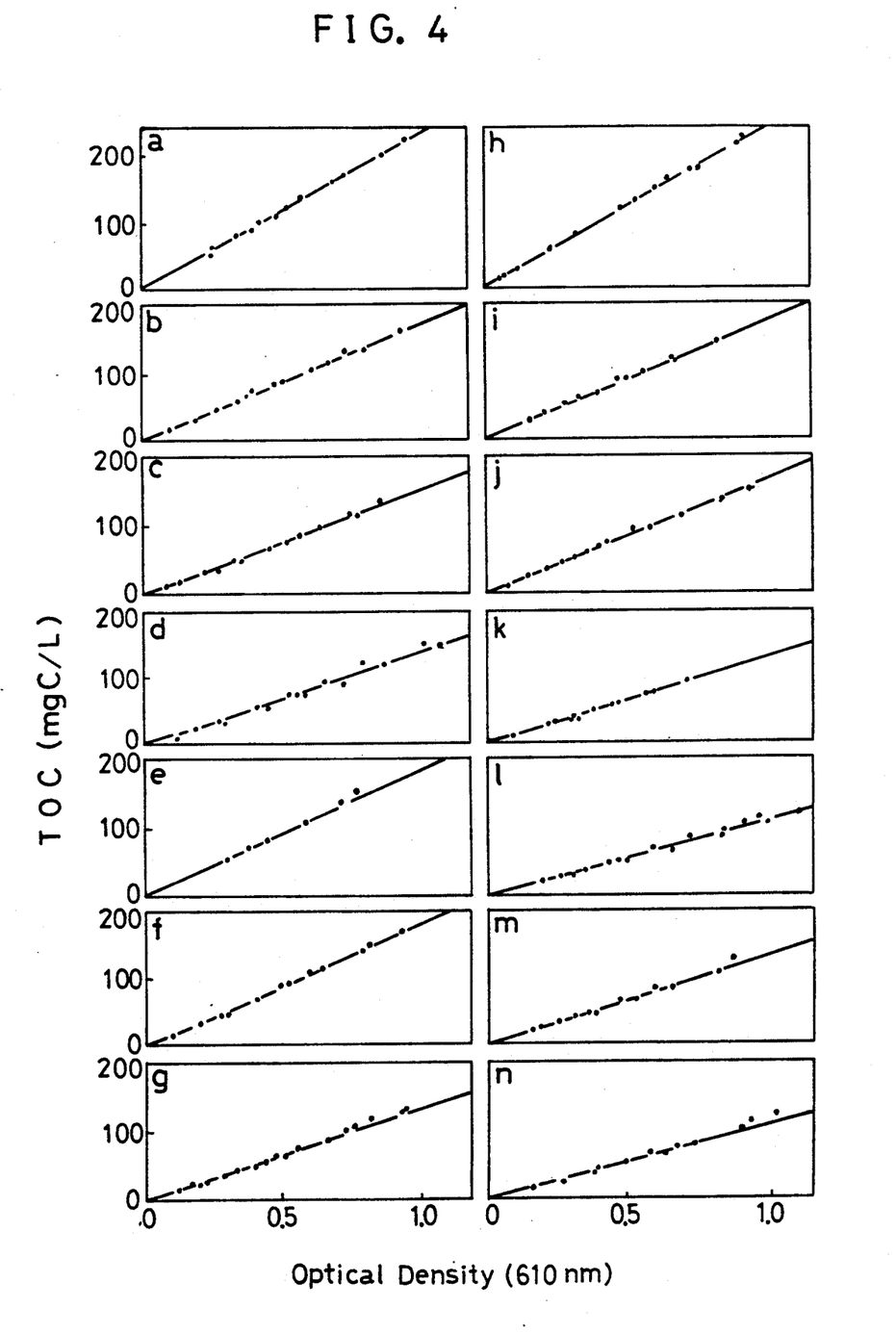
FIG. 4 is a graph showing the correlation between TOC values determined by the method of a referential example and TOC values determined according to the conventional method.

The relation between the total organic carbon (hereinafter, abbreviated as TOC) values and those obtained by the conventional optical estimation method (absorbances at 610 nm) was investigated, with regards to each of the liquors, and shown in FIG. 4. Although a proportional relation was recognized between the two kinds of values, the proportional constant was considerably different among the micro-organisms. Thus, it has been found that the TOC values can be used as a convenient means for determining micro-organisms concentrations, like as the absorbance values. Further, the TC analyser used in the experiment had a detection limit of 10 ppbC, although a detection limit of the optical density according to the above-mentioned optical estimation method was approx. 0.006 (the TOC value corresponding thereto was approx. 750 ppbC). Thus, it is evident that the quantitative determination is effected according to the present invention with a sensibility higher than that of the conventional method.

Example 3

Influence of coexisting substances on TOC values

Quantitative determination of micro-organisms was effected in the presence of glucose and glutamic acid, which may coexist as culture medium. A test liquor was prepared by adding glucose (A) and glutamic acid (B), as coexisting organic substances, to an *E. coli* suspension of a known concentration. With regard to the test liquor thus prepared, a TOC value corresponding to TC value A were determined by means of a total carbon analyser and designated $TOC_T$, and a TOC value corresponding to TC value B was determined and designated $TOC_B$. From the difference between these two values, a TOC value corresponding to the micro-organism concentration was calculated according to the following formula:

$$TOC_{Cell} = TOC_T - TOC_B.$$

The relation between the bacterium concentrations calculated according to the above formula and the known concentrations was shown in Table-1. Errors on determination was of the order of several mg C/L.

TABLE 1

| A (mg/L) | B (mg/L) | TOC (mg C/L) | | | Calculated Value[1] | Error |
| | | $TOC_T$ | $TOC_B$ | $TOC_{Cell}$ | | |
|---|---|---|---|---|---|---|
| 218 | 218 | 150 | 150 | 0 | 0 | 0 |
| 21 | 21 | 31 | 18 | 13 | 16 | 3 |
| 175 | 175 | 150 | 121 | 29 | 30 | 1 |
| 44 | 44 | 62 | 33 | 29 | 31 | 2 |
| 66 | 66 | 92 | 92 | 53 | 46 | 7 |
| 131 | 131 | 150 | 91 | 59 | 60 | 1 |
| 87 | 87 | 120 | 63 | 57 | 60 | 3 |
| 109 | 109 | 151 | 79 | 72 | 76 | 4 |
| 87 | 87 | 151 | 62 | 89 | 90 | 1 |
| 44 | 44 | 149. | 33 | 116 | 120 | 4 |
| 0 | 0 | 150 | 1 | 149 | 149 | 0 |

[1]Calculated from the known concentration

Further, the same experiments were effected with regard to those cases wherein meat extract (x) and peptone (y), which were usually used as culture medium components, were added or soluble starch (z) as an example of substances having a strong ray-scattering property was added to the above-mentioned *E. coli* suspension of a known concentration. The results obtained are shown in Table-2. Thus, it was confirmed that, by the use of a filtration method using an ultrafiltration means, influence of coexisting organic substances on TOC values could easily be excluded from the performance of determination.

TABLE 2

| (x) (mg/L) | (y) (mg/L) | (z) (mg/L) | TOC (mg C/L) | | | | |
| | | | $TOC_T$ | $TOC_B$ | $TOC_{Cell}$ | Calculated Value[2] | Error |
|---|---|---|---|---|---|---|---|
| 95 | 142 | 0 | 148 | 91 | 57 | 60 | 3 |
| 95 | 142 | 0 | 135 | 90 | 45 | 45 | 0 |
| 95 | 142 | 0 | 119 | 90 | 28 | 30 | 2 |
| 95 | 142 | 0 | 106 | 91 | 15 | 15 | 0 |
| 95 | 142 | 0 | 100 | 90 | 9 | 9 | 0 |
| 0 | 0 | 76 | 104 | 76 | 28 | 25 | 3 |
| 0 | 0 | 76 | 115 | 79 | 36 | 38 | 2 |
| 0 | 0 | 76 | 127 | 76 | 51 | 50 | 1 |

[2]Calculated from the known concentration.

Example 4

Effect of the ultrasonication of ultrafiltration means

Seven disposable filters (Nos. 1-7) same as the disposable filter used as ultrafiltration means in Example 3 were used in this evaluation. Furnishing the above-described apparatus 1 with each of these seven filters, without subjecting it to any ultrasonication treatment in super pure water (C) and after subjecting it to an ultrasonication treatment (10-60 minutes) in super pure water (D), filtration treatment of 10 cc of the specimen liquor of a known concentration was effected and elution of organic matters from the corresponding filters (C) and (D) was investigated from TOC values. The results obtained are shown in Table-3.

TABLE 3

| Filter No. | C (mg C/L) | D (mg/ C/L) |
|---|---|---|
| 1 | 0.95 | 0.39 |
| 2 | 0.72 | 0.35 |
| 3 | 0.83 | 0.47 |
| 4 | 0.75 | 0.40 |
| 5 | 0.91 | 0.43 |
| 6 | 1.98 | 0.28 |
| 7 | 1.04 | 0.44 |

From the above results, it is evident that, by subjecting each filter to an ultrasonication treatment for 10 minutes or more while being dipped in super pure water, elution of organic substances from the filter itself can be suppressed at a degree of approx. 0.4 ppm. This means that, when this kind of filter is used, the lower limit of quantitative determination can be reduced to 8 ppm. That is, the detection limit of the conventional methods can be improved by 5 times.

Example 5

Quantitative determination of micro-organisms utilizing centrifugal treatment

Microorganism-containing sample

A been yeast (Saccharomyces cerevisiae, JCM 1499) was cultivated, and then washed and diluted with a physiological salt solution (0.15 M-NaCl) to prepare a beer yeast suspension of $1.4 \times 10^7$/ml.

Conditions for combustion oxidation

Flow rate of highly pure air 150 ml/minute
Temperature of heating 680° C.

The specimen was diluted with a physiological salt solution having a carbon concentration of approx. 150 ppb, to prepare six serially diluted test liquors. Each of the diluted test liquors was introduced into a total carbon analyser, and its TC value A was calculated (injection amount: 10 μl).

Next, each of the six kinds of diluted liquors (2 ml) was subjected to a centrifugal treatment by means of a centrifuge at a rotation speed of 3500 rpm for approx. 15 minutes, and the supernatant liquor was introduced into a total carbon analyser to calculate its TC value B (injection amount: 10 μl).

From the value obtained by subtracting the TC value B from the corresponding TC value A, the carbon concentration was calculated and its correlation with the beer yeast concentration was investigated.

Further, for comparison's sake, the above determination of TC value B was effected using a treated liquor freed from micro-organisms, which was obtained from the test liquor by a suction filtration treatment, instead of the centrifugal treatment, with an injector having a disposable filter (outside diameter: 25 mm, pore diameter: 0.22 μm) made of polytetrafluoroethylene and washed by ultrasonication in pure water for approx. 20 minutes, furnished to its point. Then, the carbon concentration was calculated from this TC value B in the same manner as described above, and its correlation with the beer yeast concentration was investigated.

Figure 5:
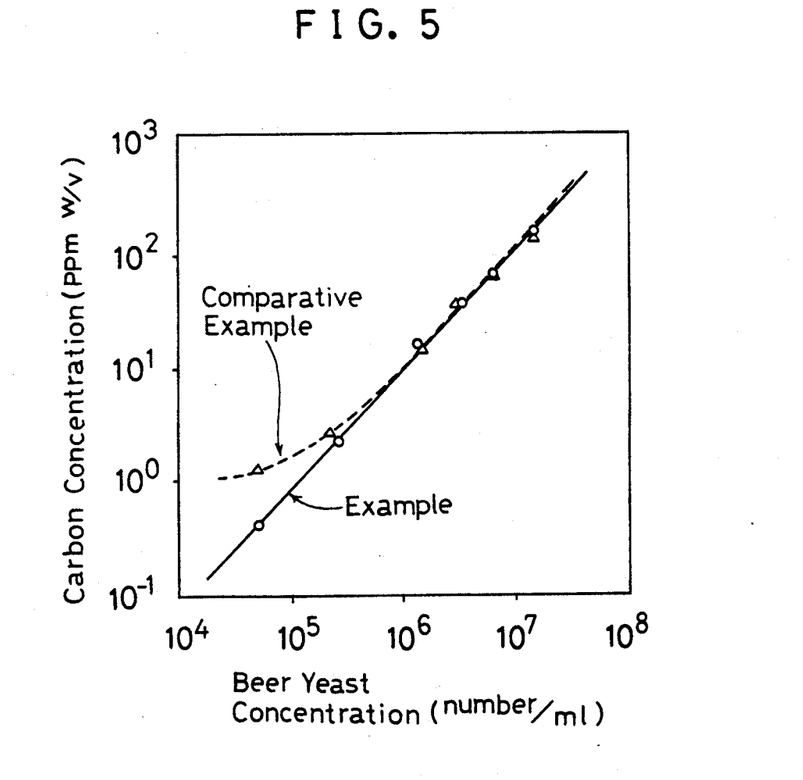
FIG. 5 is a graph showing the correlation between carbon concentrations and beer yeast concentrations obtained in an example of the present invention, together with that obtained in a comparative example.

The results obtained in the above are shown in FIG. 5, with those of the comparative examples. It is understood from these results that a good rectilineal relation between beer yeast concentrations and carbon concentrations is maintained in the Example even at a carbon concentration of 5 ppm or less, although the rectilineal relation falls in the comparative examples at a carbon concentration of 5 ppm or less. Thus, it is understood that the quantitative determination can be performed with good accuracy under the conditions of this Example, with regard to test liquors containing 5 ppm (converted into carbon concentration) or less of micro-organisms.

What we claimed is:

1. A method for the quantitative determination of micro-organisms or pyrogens which comprises introducing a first sample of a prescribed amount of a test liquor containing micro-organisms or pyrogens into a total carbon analyzer to organisms or pyrogens into a total carbon analyzer to obtain a total carbon value A, while removing micro-organisms or pyrogens from a second sample of the same said prescribed amount of the same test liquor and introducing the resultant into a total carbon analyzer to obtain a total carbon value B, subtracting the total carbon value B from the total carbon value A, and determining micro-organisms or pyrogens based upon the resulting value.

2. The method of claim 1 in which the removal for micro-organisms or pyrogens is conducted by a removal method selected from the group consisting of membrane filtration treatment method, an adsorption treatment method and a centrifugal treatment method.

3. The method of claim 2 in which the removal of microorganisms or pyrogens is conducted by a membrane filtration treatment method, and the membrane filtration treatment method is performed with a filter having a pore size of ultrafiltration grade.

4. The method of claim 3 in which the pore size is 0.45 μm or less, and suitable for removing micro-organisms.

5. The method of claim 3 in which the pore size is 0.2 μm or less, and suitable for removing pyrogens.

6. The method of claim 3 in which the filter having been treated by ultrasonic waves in super pure water is used.

7. The method of claim 2 in which the removal of microorganisms or pyrogens is conducted by a centrifugal treatment method, and the centrifugal treatment method is performed at a rotation speed of 2000–5000 rpm.

8. The method of claim 2, wherein said total carbon value A and said total carbon value B are obtained by:
  (a) sending each test liquor to a combustion tube heated at high temperature to form carbon dioxide;
  (b) transporting said carbon dioxide to a non-diffractive infra-red ray detector;
  (c) detecting absorbance of carbon dioxide; and,
  (d) calculating said total carbon value A and said total carbon value B.

* * * * *

UNITED STATES PATENT AND TRADEMARK OFFICE
CERTIFICATE OF CORRECTION

PATENT NO. : 5,116,736
DATED : May 26, 1992
INVENTOR(S) : Shu TAHARA et al.

It is certified that error appears in the above-indentified patent and that said Letters Patent is hereby corrected as shown below:

At column 1, line 65, after "test" delete ",".
At column 3, line 19, change "of of" to ---of---.
At column 3, line 37, change "680°-950°C." to ---680°-950°C---. A column 6, line 6, change "value" to ---valve---.
At column 8, line 23, change "or" to ---of---.
At column 10, line 66, change "been" to ---beer---.
At column 12, line 6 (claim 1, line 5), delete "total carbon analyzer to organisms or pyrogens into a".
At column 12, line 21 (claim 3, line 2), change "microorganisms" to ---micro-organisms---.
At column 12, line 34 (claim 7, line 2), change "microorganisms" to ---micro-organisms---.

Signed and Sealed this

Ninth Day of April, 1996

Attest:

BRUCE LEHMAN

Attesting Officer        Commissioner of Patents and Trademarks